US009813688B2

(12) United States Patent
Honda et al.

(10) Patent No.: US 9,813,688 B2
(45) Date of Patent: Nov. 7, 2017

(54) ENDOSCOPE SYSTEM, WHITE BALANCE ADJUSTMENT METHOD THEREFOR, AND IMAGE PROCESSING APPARATUS FOR ENDOSCOPE

(71) Applicant: OLYMPUS CORPORATION, Hachioji-shi, Tokyo (JP)

(72) Inventors: Kyoko Honda, Tokyo (JP); Yugo Koizumi, Yokohama (JP); Mai Ojima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/371,351

(22) Filed: Dec. 7, 2016

(65) Prior Publication Data

US 2017/0085851 A1  Mar. 23, 2017

Related U.S. Application Data

(63) Continuation of application No. PCT/JP2015/066624, filed on Jun. 9, 2015.

(30) Foreign Application Priority Data

Jun. 17, 2014 (JP) ................................. 2014-124697

(51) Int. Cl.
*A61B 1/00* (2006.01)
*A61B 1/04* (2006.01)
(Continued)

(52) U.S. Cl.
CPC ........... *H04N 9/73* (2013.01); *A61B 1/00009* (2013.01); *A61B 1/00057* (2013.01); *A61B 1/04* (2013.01);
(Continued)

(58) Field of Classification Search
CPC ... A61B 1/00009; A61B 1/04; A61B 1/00006; A61B 1/00059; A61B 1/00121; A61B 1/045; A61B 1/0638; H04N 9/73
(Continued)

(56) References Cited

U.S. PATENT DOCUMENTS

| 6,965,405 | B1* | 11/2005 | Ogino | .................... | H04N 5/772 |
| | | | | | 348/231.7 |
| 2008/0074492 | A1 | 3/2008 | Iwasaki | | |
| 2013/0141557 | A1* | 6/2013 | Kawata | .............. | A61B 1/00006 |
| | | | | | 348/65 |

FOREIGN PATENT DOCUMENTS

| JP | 2003-265410 | 9/2003 |
| JP | 2005-034166 A | 2/2005 |

(Continued)

OTHER PUBLICATIONS

Sep. 1, 2015 International Search Report issued in Patent Application No. PCT/JP2015/066624.
(Continued)

*Primary Examiner* — Nathnael Aynalem
(74) *Attorney, Agent, or Firm* — Oliff PLC (57) ABSTRACT

An endoscope system includes: an electronic endoscope that obtains an image of an inside of a subject; a first storage unit that is provided at the electronic endoscope and that stores first information, the first information including white balance data that depends on an apparatus used in the past together with the electronic endoscope; an image processing apparatus that is connected to the electronic endoscope and that applies processing to an image of the subject; a second storage unit that is provided at the image processing apparatus or a storage medium connected to the image processing apparatus and that stores second information, the second information including white balance correction data for correcting the white balance data; and a white balance
(Continued)

adjustment unit that adjusts the white balance of the image obtained by the electronic endoscope, on the basis of the first information and the second information.

5 Claims, 5 Drawing Sheets

(51) Int. Cl.
*H04N 9/73* (2006.01)
*G02B 23/24* (2006.01)
*A61B 1/045* (2006.01)

(52) U.S. Cl.
CPC .............. *A61B 1/045* (2013.01); *G02B 23/24* (2013.01); *H04N 9/735* (2013.01)

(58) Field of Classification Search
USPC ............ 348/43, 65, 68, 223.1; 600/101, 178
See application file for complete search history.

(56) References Cited

FOREIGN PATENT DOCUMENTS

| JP | 2008-073345 A | 4/2008 |
|---|---|---|
| JP | 2013-090884 A | 5/2013 |

OTHER PUBLICATIONS

Sep. 1, 2015 Written Opinion of the International Searching Authority issued in Patent Application No. PCT/JP2015/066624.
Apr. 12, 2016 Office Action issued in Japanese Patent Application No. 2016-501265.
Jul. 12, 2016 Office Action issued in Japanese Patent Application No. 2016-501265.
Oct. 18, 2016 Office Action issued in Japanese Patent Application No. 2016-501265.

\* cited by examiner

| PROCESSOR MODEL NUMBER | WB CORRECTION DATA |
|---|---|
| PA | WBP1 |
| PB | WBP2 |
| ⋮ | ⋮ |

| LIGHT SOURCE MODEL NUMBER | WB CORRECTION DATA |
|---|---|
| LA | WBL1 |
| LB | WBL2 |
| ⋮ | ⋮ |

ENDOSCOPE SYSTEM, WHITE BALANCE ADJUSTMENT METHOD THEREFOR, AND IMAGE PROCESSING APPARATUS FOR ENDOSCOPE

CROSS-REFERENCE TO RELATED APPLICATIONS

This application is based upon and claims the benefit of priority of the prior Japanese Patent Application No. 2014-124697, filed on Jun. 17, 2014, the entire contents of which are incorporated herein by reference.

This is a Continuation Application of PCT Application No. PCT/JP2015/066624, filed on Jun. 9, 2015, which was not published under PCT Article 21(2) in English.

FIELD

The present invention relates to an endoscope system, a white balance adjustment method therefor, and an image processing apparatus for an endoscope.

BACKGROUND

Conventionally, an endoscope system has been a medical system to be used in, for example, a medical institution.

An endoscope system typically includes an electronic endoscope that shoots an image of a subject, an image processing apparatus that performs various types of image processing on the shot image, and a light source apparatus that emits light to irradiate the subject via the electronic endoscope. The various types of image processing performed by the image processing apparatus include, for example, a white balance adjustment process based on white balance data obtained by a user for the electronic endoscope, the image processing apparatus, and the light source apparatus so as to optimize an image quality (e.g., hue).

The endoscope system may further include a server apparatus connected to the image processing apparatus over a network.

The following are known endoscope systems.

An electronic endoscope apparatus capable of preventing complications in a task of adjusting white balance and a decrease in color reproducibility of a subject image (see Japanese Laid-open Patent Publication No. 2005-34166). An electronic endoscope apparatus that prevents a color change in a shot image that would be caused due to time-varying spectral distribution of an illumination light source (see patent Japanese Laid-open Patent Publication No. 2013-90884).

For operations of an endoscope system, some apparatuses may be replaced with corresponding newer-generation apparatuses (what are called new apparatuses). For example, an image processing apparatus and/or a light source apparatus may be replaced with new ones. In such a case, so that an optimum image quality similar to that in the system before the replacement can be obtained after the replacement, the user needs to obtain white balance data for the electronic endoscope, image processing apparatus, and light source apparatus to be used after the replacement as white balance data to be used in the white balance adjustment process after the replacement.

SUMMARY

A first aspect of the invention provides an endoscope system that includes: an electronic endoscope that obtains an image of an inside of a subject; a first storage unit that is provided at the electronic endoscope and that stores first information, the first information including white balance data that depends on an apparatus used in the past together with the electronic endoscope; an image processing apparatus that is connected to the electronic endoscope and that applies processing to an image of the subject; a second storage unit that is provided at the image processing apparatus or a storage medium connected to the image processing apparatus and that stores second information, the second information including white balance correction data for correcting the white balance data included in the first information stored in the first storage unit; and a white balance adjustment unit that adjusts the white balance of the image obtained by the electronic endoscope, on the basis of the first information stored in the first storage unit and the second information stored in the second storage unit.

Another aspect of the invention provides a white balance adjustment method for an endoscope system that includes: an electronic endoscope that obtains an image of an inside of a subject; and an image processing apparatus connected to the electronic endoscope, the white balance adjustment method including adjusting the white balance of an image obtained by the electronic endoscope, on the basis of first information that is stored in a first storage unit provided at the electronic endoscope and that includes white balance data that depends on an apparatus used in the past together with the electronic endoscope, and second information that is stored in a second storage unit provided at the image processing apparatus or a storage medium connected to the image processing apparatus and that includes white balance correction data for correcting the white balance data included in the first information.

Still another aspect of the invention provides an image processing apparatus for an endoscope, the image processing apparatus including: a reading unit that reads first information from a first storage unit provided at an electronic endoscope, the first information including white balance data that depends on an apparatus used in the past together with the electronic endoscope; a second storage unit that stores second information, the second information including white balance correction data for correcting the white balance data included in the first information; and a white balance adjustment unit that adjusts the white balance of an image obtained by the electronic endoscope, on the basis of the first information read by the reading unit and the second information stored in the second storage unit.

DESCRIPTION OF EMBODIMENTS

The following describes embodiments of the invention by referring to the drawings.

Figure 1:
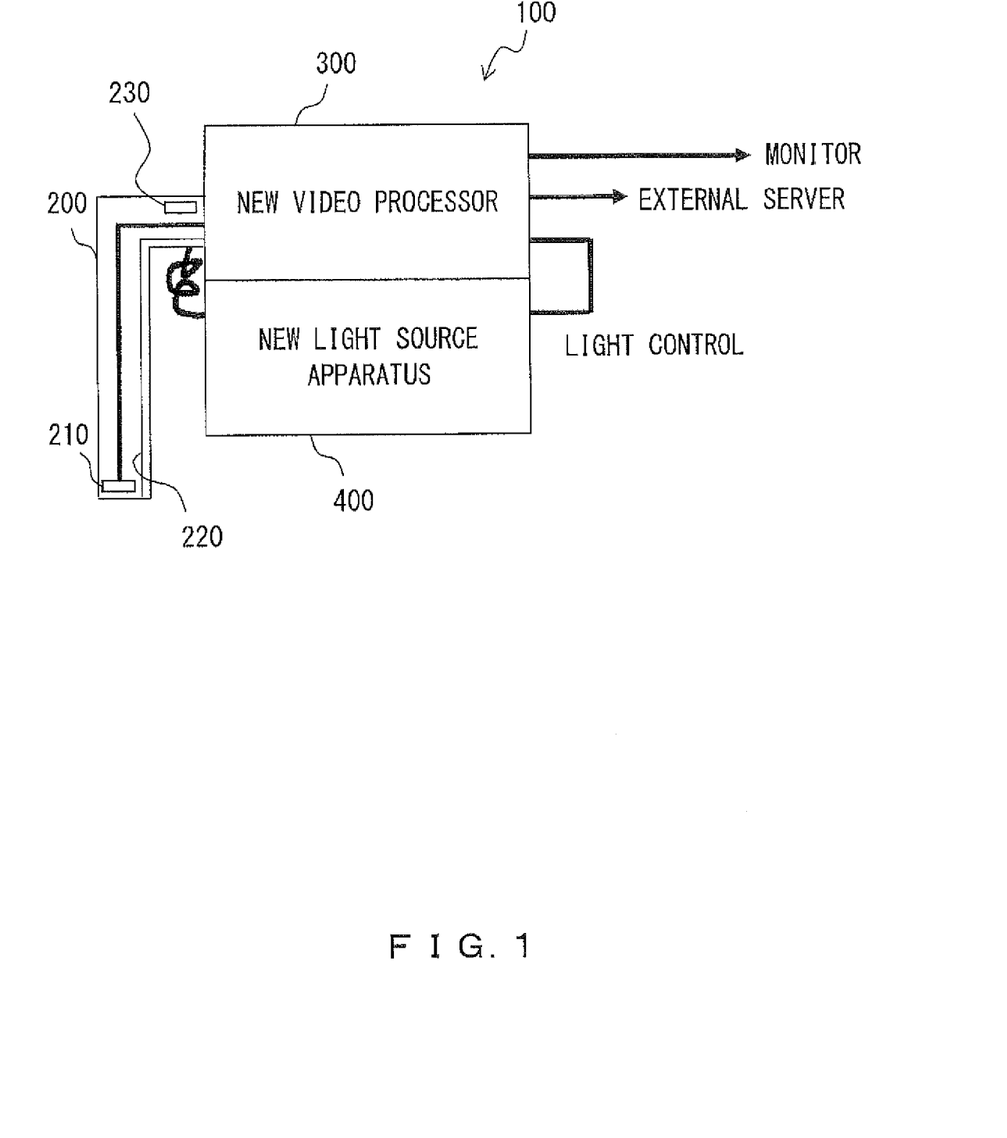
FIG. 1 illustrates an exemplary configuration of an endoscope system in accordance with an embodiment.

FIG. 1 illustrates an exemplary configuration of an endoscope system in accordance with an embodiment of the invention.

As depicted in FIG. 1, an endoscope system 100 in accordance with the present embodiment includes an electronic endoscope 200, a video processor (new video processor) 300, and a light source apparatus (new light source apparatus) 400. In the embodiment, the video processor 300 and the light source apparatus 400 are, for example, a newer-generation video processor and light source apparatus corresponding to a video processor and light source apparatus that were used in the past together with the electronic endoscope 200.

The electronic endoscope 200 includes a CCD (Charge Coupled Device) 210, a light guide 220, and a memory 230.

The CCD 210 is an exemplary image sensor and shoots an image of a subject (image shooting target).

The light guide 220 guides light emitted from the light source apparatus 400 so as to irradiate a subject.

The memory 230 is, for example, a nonvolatile memory and stores information that includes corresponding white balance data for each combination of an image processing apparatus and light source apparatus that were used in the past together with the electronic endoscope 200, as will be described in detail hereinafter with reference to FIG. 2.

The electronic endoscope 200 also includes an operation unit (not illustrated) that receives an operation instruction from a user and that reports the received operation instruction to the video processor 300.

As will be described in detail hereinafter with reference to FIG. 3, the video processor 300 performs various types of image processing on an image shot by the CCD 210 of the electronic endoscope 200. For example, the video processor 300 may output the result of the processing to a monitor (not illustrated), or may transmit the result to an external server apparatus (not illustrated) over a network (not illustrated). The video processor 300 also performs processing that corresponds to an operation instruction from a user that has been reported by the operation unit of the electronic endoscope 200. In addition to performing such operations, the video processor 300 controls operations of the entirety of the endoscope system 100.

Under light control of the video processor 300, the light source apparatus 400 emits light to irradiate a subject via the light guide 220 of the electronic endoscope 200.

Figure 2:
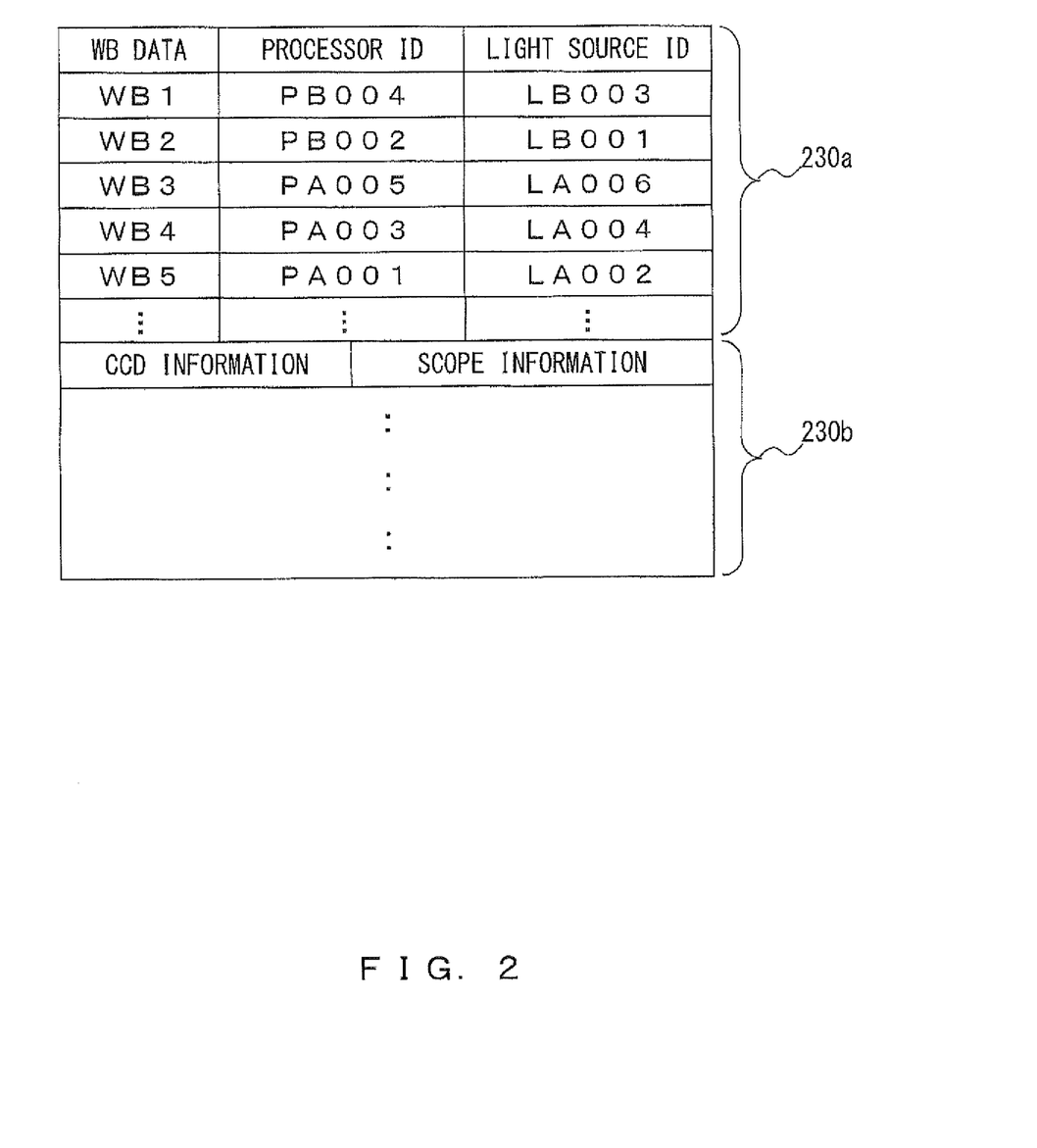
FIG. 2 illustrates an exemplary data structure of information stored in a memory of an electronic endoscope.

FIG. 2 illustrates an exemplary data structure of information stored in the memory 230 of the electronic endoscope 200.

As depicted in FIG. 2, the information stored in the memory 230 includes data 230a related to white balance and data 230b related to other items.

The data 230a related to white balance includes corresponding white balance data for each combination of a video processor and light source apparatus that were used in the past together with the electronic endoscope 200. More particularly, the data 230a includes corresponding white balance data ("WB data") for each combination of the apparatus IDs (Identifications) of a video processor and light source apparatus ("processor ID" and "light source ID") that were used in the past together with the electronic endoscope 200. Each apparatus ID is unique apparatus identification information assigned to one apparatus, and also includes the model number of the apparatus. Each piece of white balance data is obtained for the electronic endoscope 200, a video processor with a corresponding apparatus ID, and a light source apparatus with a corresponding apparatus ID. Each piece of white balance data is arranged to obtain an optimum image quality by performing a white balance adjustment process based on that piece of white balance data during use of those apparatuses. Although not illustrated, the data 230a related to white balance also includes information on a date and time at which each piece of white balance data was obtained (or a date and time at which each piece of white balance data was recorded in the memory 230).

For ease of description, a plurality of pieces of white balance data are indicated as "WB1", "WB2", "WB3", "WB4", and "WB5" in the example depicted in FIG. 2. The apparatus IDs of a plurality of video processors are also indicated as "PB004", "PB002", "PA005", "PA003", and "PA001". "PB" and "PA" indicate the model numbers of video processors. The apparatus IDs of a plurality of light source apparatuses are indicated as "LB003", "LB001", "LA006", "LA004", and "LA002". "LB" and "LA" indicate the model number of light source apparatuses.

In the example depicted in FIG. 2, "WB1" is white balance data that corresponds to a combination of a video processor with apparatus ID "PB004" and a light source apparatus with apparatus ID "LB003". "WB1" has been obtained for the electronic endoscope 200, a video processor with apparatus ID "PB004", and a light source apparatus with apparatus ID "LB003". "WB1" has been arranged to obtain an optimum image quality by performing a white balance adjustment process based on "WB1" during use of those apparatuses.

Data 230b includes information on the CCD 210 ("CCD information"), including the apparatus ID of the CCD 210, and information on the electronic endoscope 200 ("scope information"), including the apparatus ID of the electronic endoscope 200.

Figure 3:
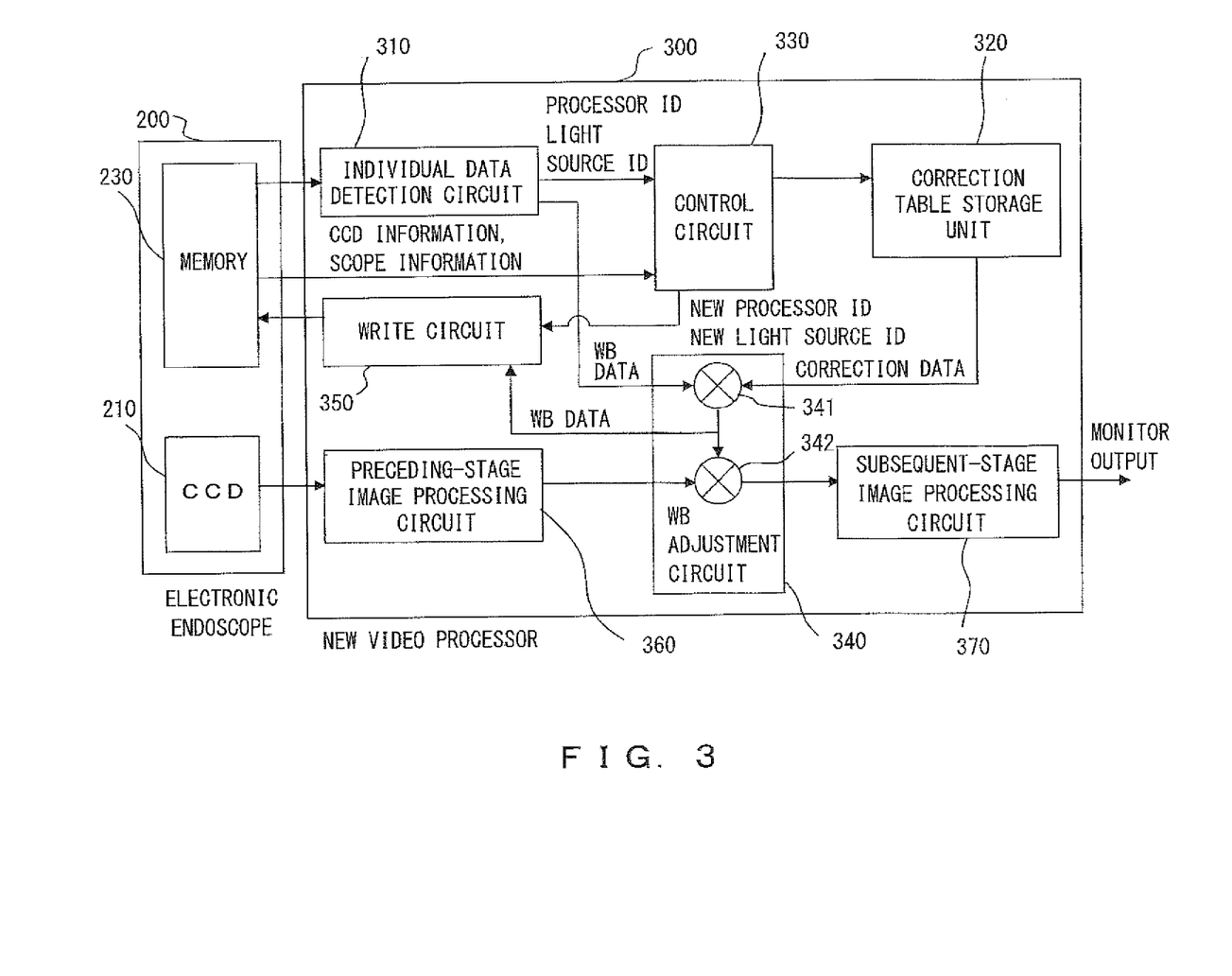
FIG. 3 illustrates an exemplary configuration of a video processor.

FIG. 3 illustrates an exemplary configuration of a video processor.

As depicted in FIG. 3, the video processor 300 includes an individual data detection circuit 310, a correction table storage unit 320, a control circuit 330, a WB (White Balance) adjustment circuit 340, a write circuit 350, a preceding-stage image processing circuit 360, and a subsequent-stage image processing circuit 370.

The individual data detection circuit 310 reads, from the memory 230 of the electronic endoscope 200, white balance data that corresponds to one combination of a video processor and light source apparatus that were used in the past together with the electronic endoscope 200. For example, the individual data detection circuit 310 may read white balance data that corresponds to one combination of a video processor and light source apparatus that were recently used together with the electronic endoscope 200. Alternatively, the individual data detection circuit 310 may read white balance data that corresponds to a combination of the latest generations among the combinations of a video processor and light source apparatus that were used in the past together with the electronic endoscope 200. In this reading process, in addition to white balance data, the apparatus IDs of a corresponding video processor and light source apparatus are read. However, when the determination result in S110 in FIG. 5, which will be described hereinafter, is Yes, only white balance data is read. The individual data detection circuit 310 outputs the read white balance data to the WB adjustment circuit 340, and outputs the read apparatus IDs of the video processor and light source apparatus to the control circuit 330.

The correction table storage unit 320 stores correction tables. The correction tables include a first correction table and a second correction table, as will be described in detail hereinafter with reference to FIG. 4. The first correction table stores information that includes corresponding white balance correction data for each video processor. The second correction table stores information that includes corresponding white balance correction data for each light source apparatus.

The control circuit 330 causes the white balance correction data that corresponds to the video-processor apparatus ID output from the individual data detection circuit 310 to be output from the correction table storage unit 320 (first correction table) to the WB adjustment circuit 340. The control circuit 330 also causes the white balance correction data that corresponds to the light-source-apparatus apparatus ID output from the individual data detection circuit 310 to be output from the correction table storage unit 320 (second correction table) to the WB adjustment circuit 340. The control circuit 330 reads information on the CCD 210 and information on the electronic endoscope 200 from the memory 230 of the electronic endoscope 200 so as to, for example, control the CCD 210 according to the apparatus ID of the CCD 210 and control the electronic endoscope 200 according to the apparatus ID of the electronic endoscope 200. The control circuit 330 outputs the apparatus IDs of the video processor 300 and the light source apparatus 400 to the write circuit 350. In addition to performing such operations, the control circuit 330 controls operations of the entirety of the endoscope system 100.

The WB adjustment circuit 340 includes two multipliers 341 and 342 and performs a white balance adjustment process. The multiplier 341 multiplies the white balance correction data that corresponds to the video-processor apparatus ID and that has been output from the correction table storage unit 320 by the white balance data output from the individual data detection circuit 310, and also multiplies the white balance correction data that corresponds to the light-source-apparatus apparatus ID and that has been output from the correction table storage unit 320 by the white balance data output from the individual data detection circuit 310. The multiplier 341 outputs the result of the multiplications to the multiplier 342 and the write circuit 350. That the multiplier 341 corrects the white balance data output from the individual data detection circuit 310 on the basis of the white balance correction data that corresponds to the video-processor apparatus ID and that has been output from the correction table storage unit 320, and the white balance correction data that corresponds to the light-source-apparatus apparatus ID and that has been output from the correction table storage unit 320. Then, the multiplier 341 outputs the corrected white balance data to the multiplier 342 and the write circuit 350. The multiplier 342 multiplies the result of the multiplication by the multiplier 341 by a result of processing by the preceding-stage image processing circuit 360, and outputs the result of this multiplication to the subsequent-stage image processing circuit 370. In particular, the multiplier 342 adjusts the white balance of an image that is the result of processing by the preceding-stage image processing circuit 360 on the basis of the corrected white balance data, and outputs the result of this processing to the subsequent-stage image processing circuit 370.

The write circuit 350 writes, to the memory 230 of the electronic endoscope 200 and as white balance data that corresponds to a combination of the video processor 300 and the light source apparatus 400, the result of the multiplication by the multiplier 341 and the apparatus IDs of the video processor 300 and the light source apparatus 400 that have been output from the control circuit 330.

The preceding-stage image processing circuit 360 performs predetermined preceding-stage image processing on an image obtained by the CCD 210 of the electronic endoscope 200, and outputs the result of the processing to the WB adjustment circuit 340.

The subsequent-stage image processing circuit 370 performs predetermined subsequent-stage image processing on the result of multiplication by the multiplier 342 of the WB adjustment circuit 340, and outputs the result of this processing to, for example, a monitor.

Figure 4:
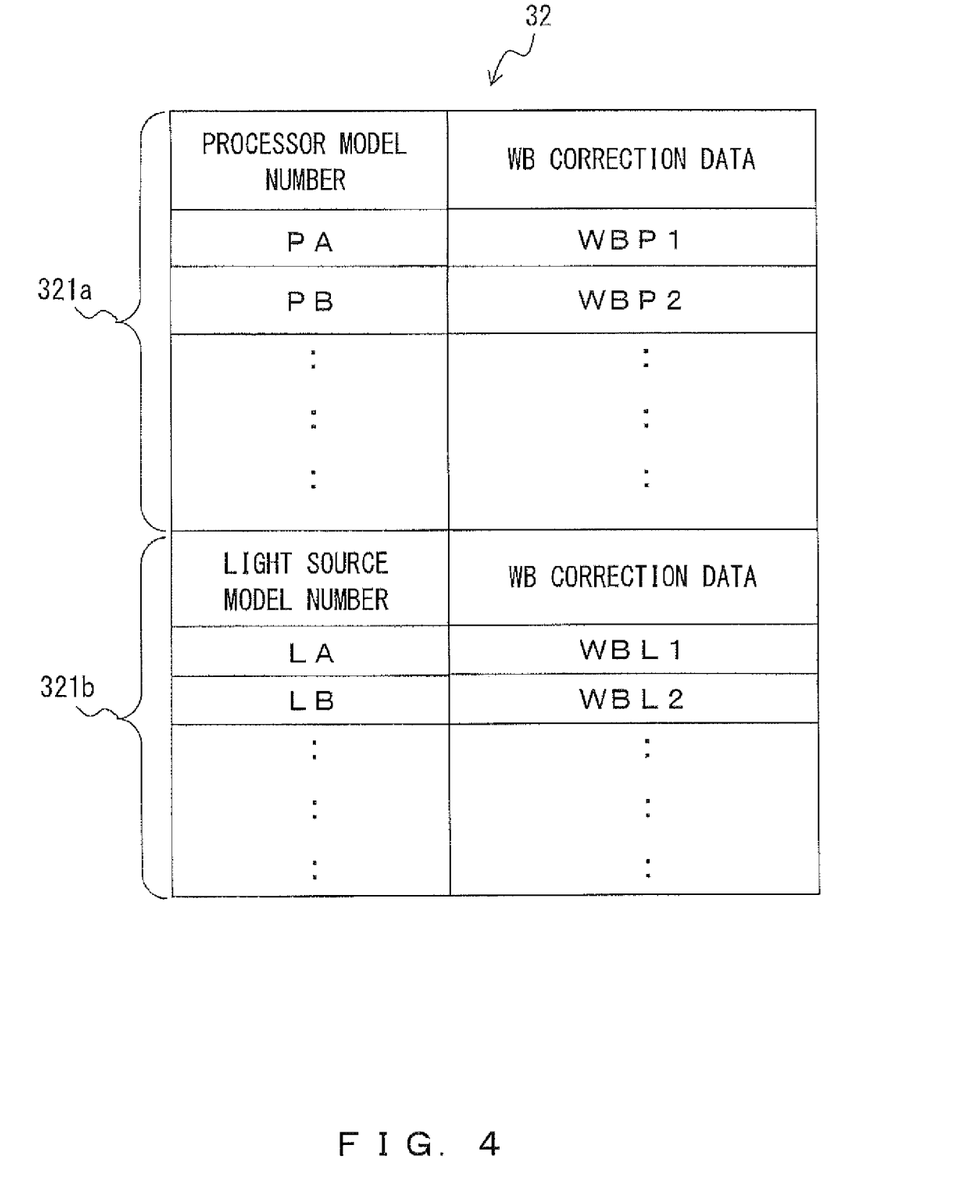
FIG. 4 illustrates an exemplary data structure of a correction table stored in a correction table storage unit.

FIG. 4 illustrates an exemplary data structure of a correction table stored in the correction table storage unit 320.

As depicted in FIG. 4, a correction table 321 includes a first correction table 321a and a second correction table 321b.

The first correction table 321a stores information that includes corresponding white balance correction data for each video processor. More particularly, the first correction table 321a stores information that includes corresponding white balance correction data ("WB correction data") for each of the model numbers of video processors ("processor model number"). Each piece of white balance correction data in the first correction table 321a is arranged in a manner such that, in replacing a video processor with a corresponding model number with the video processor 300, white balance data that has been obtained for an electronic endoscope 200 that was used before the replacement, for the video processor with the corresponding model number, and for a light source apparatus that was used before the replacement, is corrected on the basis of the piece of white balance correction data, and in a manner such that a white balance adjustment process after the replacement is performed on the basis of the corrected white balance data, thereby obtaining an optimum image quality after the replacement, as in the case before the replacement.

In the example of the first correction table 321a depicted in FIG. 4, "PA" and "PB" are indicated as model numbers of a plurality of video processors. "WBP1" and "WBP2" are also indicated as a plurality of pieces of white balance correction data.

In the example of the first correction table 321a, "WBP1" is white balance correction data that corresponds to a video processor with model number "PA". "WBP1" is arranged in a manner such that, in replacing a video processor with model number "PA" with the video processor 300, white balance data that has been obtained for an electronic endoscope 200 that was used before the replacement, for the video processor with model number "PA", and for a light source apparatus that was used before the replacement, is corrected on the basis of "WBP1", and in a manner such that a white balance adjustment process after the replacement is performed on the basis of the corrected white balance data, thereby obtaining an optimum image quality after the replacement, as in the case before the replacement.

The second correction table 321b stores information that includes corresponding white balance correction data for each light source apparatus. More particularly, the second correction table 321b stores information that includes corresponding white balance correction data ("WB correction data") for each of the model numbers of light source apparatuses ("light-source model number"). Each piece of white balance correction data in the second correction table 321b is arranged in a manner such that, in replacing a light source apparatus with a corresponding model number with the light source apparatus 400, white balance data that has been obtained for an electronic endoscope 200 that was used before the replacement, for a video processor that was used before the replacement, and for the light source apparatus with the corresponding model number is corrected on the basis of the piece of white balance correction data, and in a manner such that a white balance adjustment process after the replacement is performed on the basis of the corrected white balance data, thereby obtaining an optimum image quality after the replacement, as in the case before the replacement.

In the example of the second correction table 321b depicted in FIG. 4, "LA" and "LB" are indicated as model numbers of a plurality of light source apparatuses. "WBL1" and "WBL2" are also indicated as a plurality of pieces of white balance correction data.

In the example of the second correction table 321b, "WBL1" is white balance correction data that corresponds to a light source apparatus with model number "LA". "WBL1" is arranged in a manner such that, in replacing a light source apparatus with model number "LA" with the light source apparatus 400, white balance data that has been obtained for an electronic endoscope 200 that was used before the replacement, for a video processor that was used before the replacement, and for the light source apparatus with model number "LA" is corrected on the basis of "WBL1", and in a manner such that a white balance adjustment process after the replacement is performed on the basis of the corrected white balance data, thereby obtaining an optimum image quality after the replacement, as in the case before the replacement.

In the configuration of the endoscope system 100 described above, the memory 230 of the electronic endoscope 200 is an example of the first storage unit; a region of the correction table storage unit 320 in which is stored the first correction table 321a is an example of the second storage unit; a region of the correction table storage unit 320 in which is stored the second correction table 321b is an example of the third storage unit; the individual data detection circuit 310 of the video processor 300 is an example of the reading unit; the WB adjustment circuit 340 of the video processor 300 is an example of the white balance adjustment unit; the write circuit 350 of the video processor 300 is an example of the writing unit.

The following describes operations of the endoscope system 100 in accordance with an embodiment.

In the following, descriptions are given of the following one of such operations: an operation performed when the video processor 300 and the light source apparatus 400 have been connected to the electronic endoscope 200.

Figure 5:
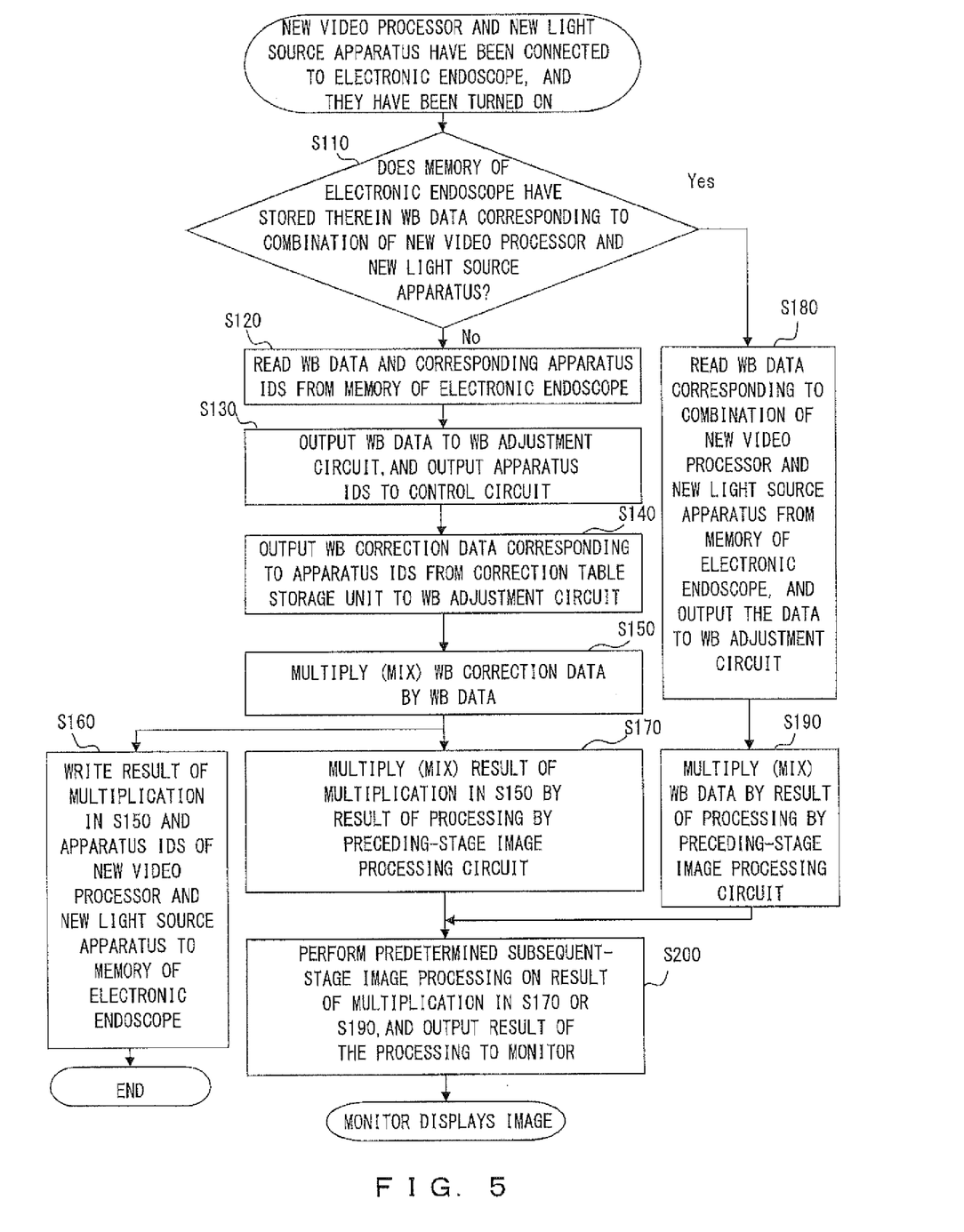
FIG. 5 is a flowchart illustrating an exemplary operation performed when a video processor and a light source apparatus have been connected to an electronic endoscope.

FIG. 5 is a flowchart illustrating an example of such an operation.

The operation starts when the video processor (new video processor) 300 and the light source apparatus (new light source apparatus) 400 have been connected to the electronic endoscope 200 and the apparatuses have been turned on, as depicted in FIG. 5.

Once the operation starts, the video processor 300 determine whether white balance data corresponding to a combination of the video processor 300 and the light source apparatus 400 has been stored in the memory 230 of the electronic endoscope 200 (S110). This determination also determines whether this is the first time the video processor 300 and the light source apparatus 400 have been connected to the electronic endoscope 200. That is, a judgment result of No in S110 means that that connection is the first one; a judgment result of Yes in S110 means that that connection is not the first one (the second or following connection). The first connection indicates, for example, that it is a situation just after a video processor and light source apparatus that had been used together with the electronic endoscope 200 have been replaced with the video processor 300 and the light source apparatus 400.

When the judgment result of S110 is No, the individual data detection circuit 310 of the video processor 300 reads white balance data corresponding to one combination of a video processor and a light source apparatus from the memory 230 of the electronic endoscope 200, together with the apparatus IDs of the video processor and the light source apparatus (S120). In this example, the individual data detection circuit 310 reads white balance data obtained on the latest date and time (or recorded on the latest date and time) together with corresponding apparatus IDs (the apparatus IDs of the video processor and the light source apparatus).

After S120, the individual data detection circuit 310 outputs the read white balance data to the WB adjustment circuit 340, and outputs the read apparatus IDs of the video processor and the light source apparatuses to the control circuit 330 (S130).

After S130, the control circuit 330 causes white balance correction data corresponding to the apparatus ID of the video processor that has been output from the individual data detection circuit 310 in S130, and white balance correction data corresponding to the apparatus ID of the light source apparatus that has been output from the individual data detection circuit 310, to be output from the correction table storage unit 320 to the WB adjustment circuit 340 (S140). The white balance correction data corresponding to the apparatus ID of the video processor that has been output from the individual data detection circuit 310 refers to white balance correction data corresponding to a model number included in the apparatus ID of the video processor. The white balance correction data corresponding to the apparatus ID of the light source apparatus that has been output from the individual data detection circuit 310 refers to white balance correction data corresponding to a model number included in the apparatus ID of the light source apparatus. When, for example, the individual data detection circuit 310 has output in S130 "PB004" and "LB003" (FIG. 2) as the apparatus IDs of the video processor and the light source apparatus, "WBP2" and "WBL2", which respectively correspond to the "PB" and "LB" in FIG. 4, are output to the WB adjustment circuit 340.

After S140, the WB adjustment circuit 340 causes the multiplier 341 to multiply the white balance data that has been output from the individual data detection circuit 310 in S130 individually by the white balance correction data corresponding to the apparatus ID of the video processor that has been output from the correction table storage unit 320 in S140, and by the white balance correction data corresponding to the apparatus ID of the light source apparatus that has been output from the correction table storage unit 320 in S140 (S150). This mixes the white balance data that has been output from the individual data detection circuit 310 individually with the white balance correction data corresponding to the apparatus ID of the video processor that has been output from the correction table storage unit 320, and with the white balance correction data corresponding to the apparatus ID of the light source apparatus that has been output from the correction table storage unit 320. That is, the white balance data output from the individual data detection circuit 310 is corrected on the basis of the white balance correction data corresponding to the apparatus ID of the video processor that has been output from the correction table storage unit 320, and the white balance correction data corresponding to the apparatus ID of the light source apparatus that has been output from the correction table storage unit 320.

After S150, the processes of S160 and S170 are performed in parallel. Although those processes are performed in parallel in this example, they may be performed in series.

In S160, the write circuit 350 writes, to the memory 230 of the electronic endoscope 200 and as white balance data corresponding to a combination of the video processor 300 and the light source apparatus 400, the multiplication result from S150 (corrected white balance data) and the individual apparatus IDs of the video processor 300 and the light source apparatus 400 that have been output from the control circuit 330. After S160, the process ends.

In S170, the WB adjustment circuit 340 causes the multiplier 342 to multiply the result of the multiplication in S150 by a result of processing by the preceding-stage image processing circuit 360. This mixes the result of the multiplication in S150 with a result of processing by the preceding-stage image processing circuit 360. That is, the white balance of an image that is the result of processing by the preceding-stage image processing circuit 360 is adjusted on the basis of the corrected white balance data that is the result of the multiplication in S150. Note that the result of processing by the preceding-stage image processing circuit 360, or an image that is the result of processing by the preceding-stage image processing circuit 360, is an image obtained by the preceding-stage image processing circuit 360 performing preceding-stage image processing on an image that has been shot by the CCD 210 of the electronic endoscope 200.

Meanwhile, when the judgment result of S110 is Yes, the individual data detection circuit 310 of the video processor 300 reads white balance data corresponding to a combination of the video processor 300 and the light source apparatus 400 from the memory 230 of the electronic endoscope 200. The individual data detection unit 310 outputs the white balance data to the WE adjustment circuit 340 (S180).

After S180, the WB adjustment circuit 340 causes the multiplier 342 to multiply the white balance data output in S180 by the result of the processing by the preceding-stage image processing circuit 360 (S190). This mixes the white balance data read in S180 with a result of processing by the preceding-stage image processing circuit 360. That is, the white balance of an image that is the result of processing by the preceding-stage image processing circuit 360 is adjusted on the basis of the white balance data read in S180. Note that the result of processing by the preceding-stage image processing circuit 360, or an image that is the result of processing by the preceding-stage image processing circuit 360, is the same as the one described above with reference to S170.

After S170 or S190, the subsequent-stage image processing circuit 370 performs predetermined subsequent-stage image processing on the result of the multiplication from S170 or that from S190, and outputs the result of the processing to a monitor (S200). Then, the monitor displays the image.

As described above, the endoscope system 100 in accordance with the present embodiment is such that, in replacing a video processor and light source apparatus that have been used together with the electronic endoscope 200 with a newer-generation video processor 300 and a newer-generation light source apparatus 400, white balance data is automatically obtained for the electronic endoscope 200, the video processor 300, and the light source apparatus 400 that are to be used after the replacement. In addition, the white balance adjustment process after the replacement is performed on the basis of the white balance data. This eliminates burdens that would be imposed on the user in association with the replacement.

Various changes can be made to the endoscope system 100 in accordance with the embodiment.

As an example, the correction table 321 stored in the correction table storage unit 320 of the video processor 300 may be updated by an external server apparatus over a network on an as-needed basis.

As another example, the correction table storage unit 320 of the video processor 300 may be a portable memory connectable/disconnectable to/from the video processor 300. In this case, the correction table 321 may be updated by replacing the portable memory. The portable memory is, for example, a transportable recording medium described hereinafter. The video processor 300 includes a medium reading apparatus to which the transportable recording medium is connectable.

For example, operations achieved by hardware for the video processor 300 may be achieved by software. In this case, the video processor 300 includes a CPU (Central Processing Unit), a ROM (Read Only Memory), and a RAM (Random Access Memory), and a program from the ROM may be stored in the RAM and executed by the CPU, thereby achieving the operations. Alternatively, the program may be obtained from, for example, an external server apparatus connected to a network, and may be stored in the RAM and executed by the CPU. Alternately, the video processor 300 may include, for example, a medium reading apparatus; the program may be obtained from a transportable recording medium connected to the medium reading apparatus, and may be stored in the RAM and executed by the CPU. As the transportable recording medium, various forms of recording media can be used, e.g., a CD-ROM (Compact Disc Read Only Memory), a flexible disk, an optical disk, a magneto-optical disk, a DVD (Digital Versatile Disc), and a USE memory.

As described above, on the basis of the present embodiment, in replacing an image processing apparatus and/or a light source apparatus with corresponding newer-generation apparatuses, white balance data is automatically obtained in association with the replacement, thereby eliminating burdens that would be imposed on the user in association with the replacement.

The embodiments described above indicate specific examples of the present invention to facilitate understanding of the invention. The invention is not limited to the embodiments described above. Various modifications and changes can be made to the invention without departing from the idea of the invention defined in the claims.

What is claimed is:

1. An endoscope system comprising:
   an electronic endoscope that obtains an image of an inside of a subject and stores first information, in a memory of the electronic endoscope, including white balance data based on a combination of information from an older-generation image processing apparatus and an older-generation light source apparatus previously used together with the electronic endoscope;
   a newer-generation light source apparatus that emits light to irradiate the subject; and
   a newer-generation image processing apparatus that: (i) connects to the electronic endoscope, (ii) processes the image of the subject, and (iii) includes one or more processors programmed to:
      store second information, in a memory of the newer-generation image processing apparatus, including white balance correction data corresponding to the newer-generation image processing apparatus and the newer-generation light source apparatus; and correct and adjust the white balance of the image obtained by the electronic endoscope based on corresponding data included in the first information and the second information, such that the electronic endoscope operates with the newer-generation image processing apparatus and the newer-generation light source apparatus by providing the first information stored in the memory of the electronic endoscope from the older-generation image processing apparatus and the older-generation light source apparatus previously used with the electronic endoscope.

2. The endoscope system according to claim 1, wherein the white balance data and the white balance correction data correspond to a combination of the newer-generation image processing apparatus and the newer-generation light source apparatus to be used together with the electronic endoscope.

3. The endoscope system according to claim 2, wherein the white balance correction data corresponds to a combination of information from the newer-generation image processing apparatus and the newer-generation light source apparatus that correspond to the older-generation image processing apparatus and the older-generation light source apparatus previously used with the electronic endoscope.

4. The endoscope system according to claim 1, wherein the one or more processors write the adjusted white balance data to the memory of the electronic endoscope as white balance data corresponding to the combination of the newer-generation image processing apparatus and the newer-generation light source apparatus.

5. The endoscope system according to claim 1, wherein the one or more processors use a multiplication result to adjust the white balance data written to the memory of the electronic endoscope, the multiplication result being a result obtained by multiplying the white balance correction data based on the second information by the white balance data based on the first information.

* * * * *